US00PP12123P2

(12) United States Plant Patent
Sperling

(10) Patent No.: US PP12,123 P2
(45) Date of Patent: Oct. 2, 2001

(54) *MANDEVILLA×AMABILIS* CULTIVAR MONITE

(76) Inventor: Joe Sperling, 4839 La Vella Dr., Oak Park, CA (US) 91377

( * ) Notice: Subject to any disclaimer, the term of this patent is extended or adjusted under 35 U.S.C. 154(b) by 0 days.

(21) Appl. No.: 09/592,233

(22) Filed: Jun. 12, 2000

(51) Int. Cl.[7] ..... A01H 5/00
(52) U.S. Cl. ..... Plt./232

(58) Field of Search ..... Plt./232

*Primary Examiner*—Bruce R. Campell
*Assistant Examiner*—Susan B. McCormick

(57) ABSTRACT

A new and distinct selection of *Mandevilla×amabilis* cultivar Monite characterized by its unique combination of pale pink buds and pale pink flowers which display a showy cluster of pink petaloids within the flower throat appearing as a pink flower within a larger pale pink flower.

2 Drawing Sheets

This invention relates to a new and distinct selection of *Mandevilla×amabilis* (Hort. Bach.) Dress., reputed to be a hybrid of *Mandevilla speldens×Mandevilla crassinoda* and a member of the Apocynaceae family. *Mandevilla×amabilis* cultivar Monite was the result of a sport observed on a *Mandevilla×amabilis* cultivar Alice du Pont (not patented) plant in April 1997. This novelty of a flower within a flower which botanically are the petaloids within the throat of the flower, was what the selection was based on. My discovery was made at Sperling Landscape & Supply, 24460 Calabalas Road, Calabalas, Calif. My new selection has been asexually reproduced at 18331 East Foothill Boulevard, Azusa, Calif. exclusively by tissue culture since the discovery. Had this sport not been discovered and propagated, it may have been lost to mankind. It is unlikely this particular select and favourable attribute of this plant could be conveyed to progeny through sexual reproduction in the next generation. Through extensive tissue culture propagation it has been established that the novel exceptional characteristics of this plant are stable and reliably passed on to clonal specimens through asexual reproduction.

SUMMARY OF THE INVENTION

*Mandevilla×amabilis* cv. Monite was selected for its showy cluster of pink petaloids within the flower throat appearing as a pink flower within a larger pale pink flower. Prior to my discovery, only *Mandevilla×amabilis* with either single flowers such as *Mandevilla×amabilis* c.v. Alice du Pont (not patented), c.v. Monte U.S. Plant Pat. No. 10,329, and c.v. White Delite U.S. Plant Pat. No. 8,479 along with the recently introduced double c.v. Rita Marie Green U.S. Plant Pat. No. 11,787 were widely grown. None of these cultivars display showy petaloids that remain within the throat of the flower. My selection cultivar Monite will tolerate a 30° F. temperature, which is equivalent to U.S.D.A. hardiness zone ten, but does require frost protection.

BRIEF DESCRIPTION OF ILLUSTRATION

The accompanying illustrations FIG. 1 and FIG. 2 exhibit flowers and buds of a specimen of cultivar Monite reproduced in color as true as reasonably possible with illustrations of this type, the color fidelity may be slightly lighter in color.

BOTANICAL DESCRIPTION

Below is a detailed description of a 2 year old plant of *Mandevilla×amabilis* cultivar Monite. The color terminology is from The Royal Horticultural Color Charts. Descriptions are from containerized plants grown in temperatures ranging from 35° F. to 105° F. in Azusa, Calif.

Overall habit: Tropical twining vine.

Overall size: Average height is 5 meters, may achieve height to 6–7 meters. Similar in overall size to other *Mandevilla×amabilis* cultivars.

Root development: Nine weeks from agar media to fully rooted through tissue culture process.

Heat/drought tolerance: Thrives in temperatures 75° F. to 105° F. with ample soil moisture. Prefers roots and base in shaded situation.

Pest/disease resistance: Similar to 'Alice du Pont' variety, susceptible to red spider mites.

FOLIAGE

Leaf arrangement: Opposite.
Type: Evergreen.
Shape: Elliptic.
Length: 10 cm to 16.5 cm.
Width: 5 cm to 7 cm.
Margins: Entire.
Apex: Short acuminate to tapered long acuminate.
Base: Cordate.
Texture: Coriaceous.
Venation: Lightly sunken veins appearing slightly bullate, one ribbed, secondary venation perpendicular to primary vein, curving upward.
Color:
*Mature foliage.*—Upper Leaf Surface: Green Group 137A. Lower Leaf Surface: Yellow Green Group 146B. Upper Midrib: Yellow Green Group 144B. Lower Midrib: Yellow Green Group 145C.
*Juvenile foliage.*—Upper Leaf Surface: Yellow Green Group 146B. Lower Leaf Surface: Yellow Green Group 146B, 146C mixed with 63B Red Purple Group. Upper Midrib: Yellow Green Group 146D. Lower Midrib: Yellow Green Group 145D mixed with Red Purple Group 63B.

PETIOLE

Length: 8 mm to 12 mm.
Diameter: 4 mm to 6 mm.
Color: Yellow Green Group 144B to Green Group 138B.

STEM

Diameter: 4 mm on new growth to 14 mm on mature growth.
Color: Juvelile, Yellow Green Group 144A; Mature Grey Brown Group 199A.
Internode length: Grown in full sun, varies 4 to 8 cm.
Internode texture: Smooth on mature stems, pubescent on juvenile stem.

FLOWERS

Arrangement: Axillary raceme, 16 to 24 flowers per raceme.
Bloom season: Flowers produced Spring through Fall.
Number of flowers at anthesis: generally 2–3 flowers opened on each raceme during bloom season.
Structure: Funnel shaped.
*Outer.*—5 parted corolla limbs.
*Inner.*—5 parted petaloids.
Bud:
*Length.*—5.5 cm to 6 cm.
*Width.*—1.6 cm to 2 cm.

COROLLA

Shape at anthesis: Corolla lobes overlap, with a length of 15 mm to 20 mm in depth where the lobes do not overlap.
Width: 8.5 cm to 10 cm.
Length of throat from calyx to corolla limb attachment: 4 cm–4.5 cm.
Length of corolla from calyx to top of corolla: 5 cm–6 cm.
Margins: Entire.
Texture: Glabrous.
Individual corolla limbs: 3.5 cm–4.5 cm long 3 cm–4 cm wide.
Shape: Asymmetrical lobes with straight margin on one side, rounded on opposite side, overlapping.

CALYX

Sepal number: 5.
Length: 5 mm length, 2–3 mm in width at base, narrowing to 1 mm at tip.
Shape: Wide acicular.
Texture: Glabrous.
Color: Yellow Green Group 145A, tip edged with Red Purple Group 63B.

PETALOIDS

Number: Derived from 5 vestriges of stamens. Petaloid number approximately 10–15 lobes.
Individual petaloid length: 3–3.5 cm.
Individual petaloid width: 2–4 cm.
Texture: Glabrous.
Petaloid attachment: 1.4–1.7 cm above the top of calyx, petaloids sometimes joined at base or maybe separated the first 3 mm then usually joined together at minimum 5 mm–1.2 cm in length overall shape: petaloids are tightly clustered and appear within the corolla throat not exceeding 1 cm above corolla limb attachment exhibiting "a flower within a flower".
Individual petaloid shape: Varying in shape with obovate broad deeply cut showy petaloids attached to reminants with little or no vestige of stamen visible and showy broad petaloids.
Color:
*Bud.*—Closed prior to anthesis Red-Purple 62B at tips and margins, Red Purple 65D outside corolla tube suffused with Yellow Green 145D lower 2 to 2.5 cm of corolla tube.
*Corolla and petaloids.*— Red Purple 65B & C on margins lightening in color to Red Purple 65D suffused with White Group 155D with tips of corolla lobes and tips of petaloids tinged with Red-Purple 65D.
*Corolla throat.*—Slightly darkened striations of Red-Purple 65C changing to Yellow Group 4B at inner 12 mm of base (not visible on illustration).
*Petaloid throat.*—Margins appear the darkest shade of Red Purple 65B and 65C as do the stamen vestiges and portion above the Yellow base (not visible on illustration). Changing to Yellow Group 4B at inner base, 7 mm of bottom.
*Lastingness of bloom.*—Minimum of five days.
*Fragrance.*—No fragrance.

REPRODUCTIVE STRUCTURES

Pistil: Superior.
Style: Generally present 10 to 15 mm in length, 1 mm to 2 mm in width Color: Yellow Green Group 145B.
Stigma: Visible, 2 mm long, 2 mm width Color: Yellow Green Group 145C.
Stamens: Absent or vestiges of stamens present surrounded by showy petaloids (see description of petaloids).
Fruit: None observed—to date my new selection has not produced fruit/seed.

I claim:

1. A new selection of Mandevilla plant substantially as herein shown and described.

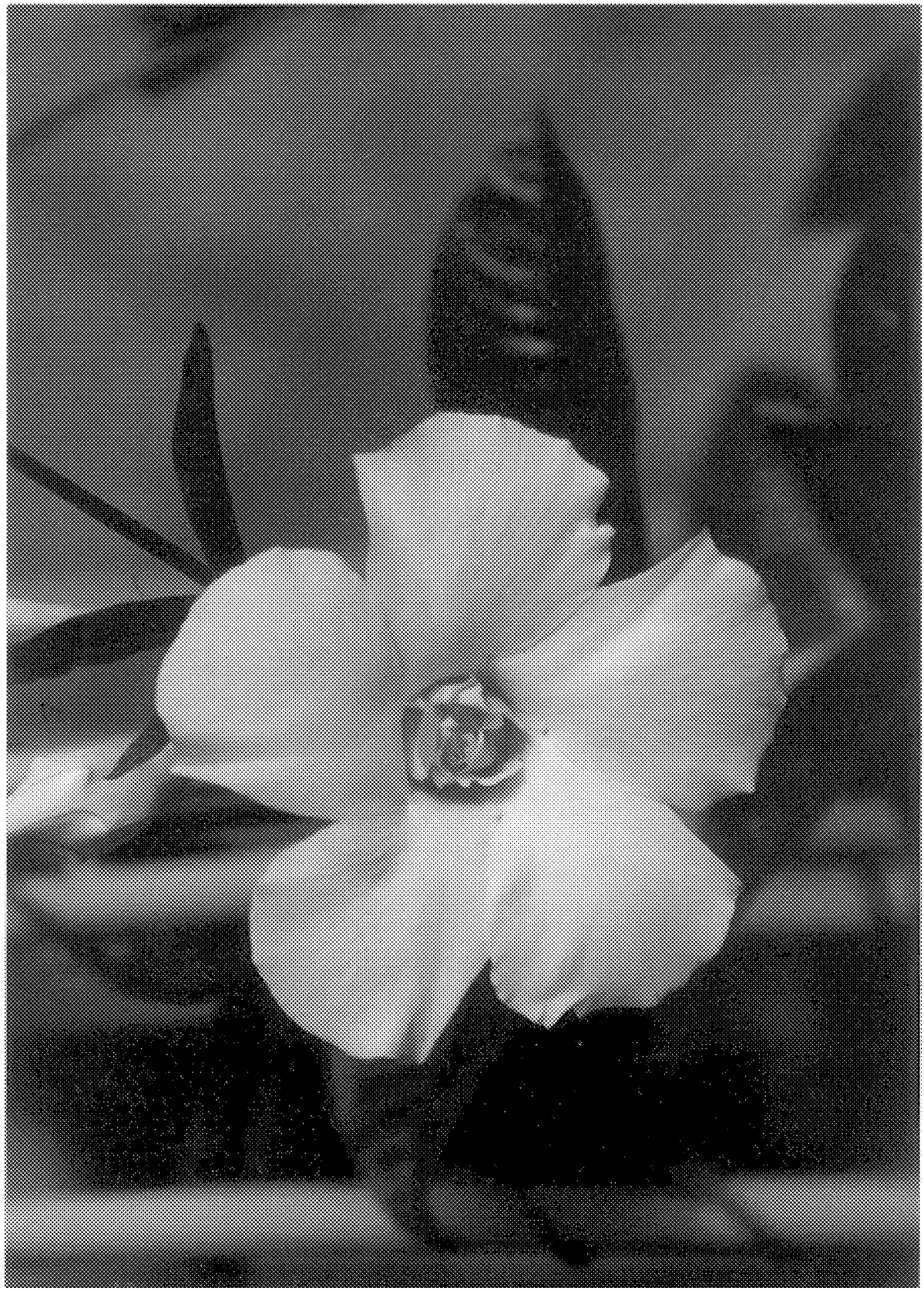

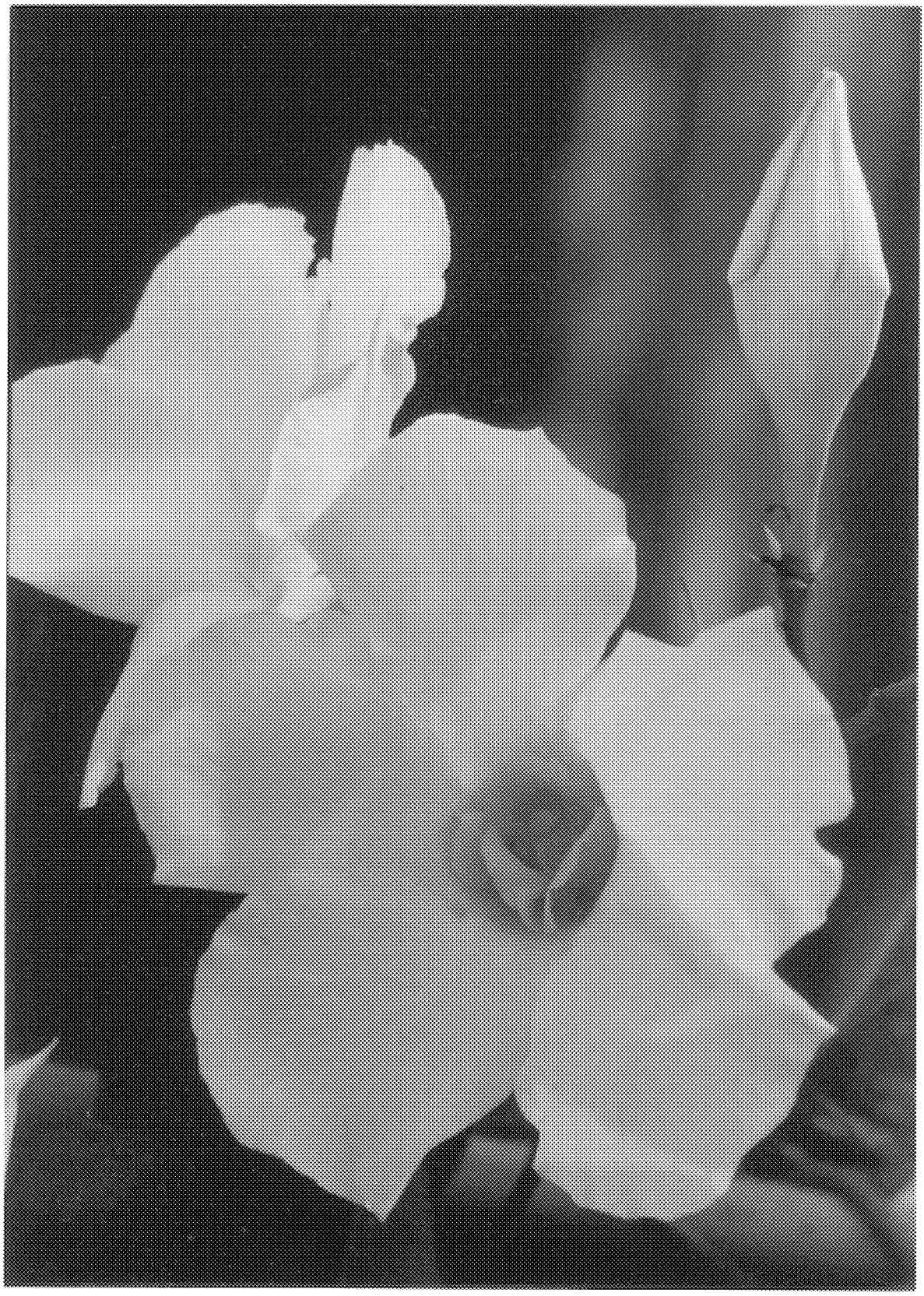

* * * * *